United States Patent [19]

Baughn

[11] Patent Number: 4,912,980
[45] Date of Patent: Apr. 3, 1990

[54] MODULAR TEST FIXTURE FOR VIBRATION AND SHOCK TESTING

[75] Inventor: Daniel L. Baughn, San Dimas, Calif.

[73] Assignee: Team Corporation, South El Monte, Calif.

[21] Appl. No.: 280,230

[22] Filed: Dec. 5, 1988

[51] Int. Cl.$^4$ .......................................... G01N 29/00
[52] U.S. Cl. ....................................................... 73/663
[58] Field of Search ................... 73/570, 573, 663, 662

[56] References Cited

U.S. PATENT DOCUMENTS

| | | | |
|---|---|---|---|
| 3,670,563 | 6/1972 | Light | 73/663 |
| 4,603,587 | 8/1986 | Kimball et al. | 73/663 |
| 4,735,089 | 4/1988 | Baker et al. | 73/663 |

Primary Examiner—Stewart J. Levy
Assistant Examiner—Louis M. Arana
Attorney, Agent, or Firm—Christie, Parker & Hale

[57] ABSTRACT

A modular test fixture for use in vibration and shock testing of printed circuit cards comprises a plurality of separate generally planar card-mounting plates each having a two-dimensional array of uniformly spaced apart mounting holes within a rectangular rigid outer frame extending around the outer boundary of each plate. Printed circuit cards of varying sizes are affixed to the mounting plate by clamps positioned along opposite edges of each card, with spaced apart fasteners along each clamp being aligned with and fastened to preselected mounting holes on the plate. The individual card-mounting plates, with the circuit cards attached thereto, are stacked together to form a rigid multi-layer fixture sufficient for vibration and shock testing of the circuit cards mounted at different levels within the fixture. The resulting fixture is fastened to an external shaker for imparting shock and vibration loads to the fixture for use in testing the circuit cards for screening and solder joint defects.

45 Claims, 4 Drawing Sheets

MODULAR TEST FIXTURE FOR VIBRATION AND SHOCK TESTING

FIELD OF THE INVENTION

This invention relates to test fixtures, and more particularly to a modular test fixture that can be used for simultaneously testing circuit cards, or other components of various sizes for shock and vibration.

BACKGROUND OF THE INVENTION

Printed circuit cards, for example, are commonly tested for defects before they are used. These defects can arise from screening or solder joint problems. Defects are tested for by simulating the environment in which the circuit card will be used. For instance, in aerospace applications, such as for the Space Shuttle, circuit cards are tested under conditions simulating actual environmental conditions of high pressure, temperature, moisture, high vibration and shock.

In the past, high vibration and shock have been tested by placing the circuit cards, or other components in various types of test fixtures which are then attached to a shaker. The fixture can be arranged for testing six-axis shock and three-axis vibration in a typical test for screening or solder joint problems in the circuit boards under test.

One prior art test fixture comprises a box with a door which opens into a hollow interior region for mounting the circuit cards. The circuit cards under test slide into fixed slots on opposite sides of the test fixture interior. The door of the fixture is then closed, and the fixture is subjected to shock and vibration testing. This fixture has several disadvantages. For instance, the fixed slots within the fixture are useful in only mounting individual cards of the same size. If a board failure develops, the circuit card can slide out and be replaced; but the fixture uses hydraulics for locking the door and clamping onto the boards, and hydraulics can be a source of contamination. The fixture is generally hollow with no internal support for the cards which are subject to undesired bending loads during vibration testing.

The present invention provides a test fixture which overcomes these problems and also provides additional improvements described below.

SUMMARY OF THE INVENTION

Briefly, one embodiment of this invention provides a modular test fixture for use in testing vibration and shock for printed circuit cards, or other components. A plurality of separate generally planar card-mounting plates are used in the test fixture. Each plate has a card-mounting surface within the confines of an outer boundary of the card-mounting plate. A preselected number of circuit cards of varying sizes can be rigidly secured to the card-mounting surface for holding the circuit cards generally within the plane and within the outer boundary of the card-mounting plate. A plurality of the card-mounting plates each with the circuit cards fastened to them, are stackable one upon the other to form a multi-layer fixture containing circuit cards at different levels within the fixture. The stacked card-mounting plates are rigidly secured together as a unit sufficient for vibration and shock testing of the circuit cards mounted within the fixture. The resulting fixture is adapted for fastening to an external shaker for imparting shock and vibration to the fixture for use in testing the circuit cards mounted to the fixture.

In a preferred form of the invention, each card-mounting plate has an two-dimensional array of mounting holes in alignment with fastening means carried on separate card-mounting clamps. The card-mounting clamps are secured to opposite edges of circuit cards of varying sizes and fastened to the array of mounting holes for custom-mounting circuit cards of varying sizes within the confines of the outer boundary of each card-mounting plate. Thus, each circuit card is independently and rigidly secured to a rigid card-mounting plate within the fixture, and all card-mounting plates are fastened together as a rigid unit suitable for vibration and shock testing. The fixture allows testing of various size boards simultaneously; each card is isolated physically to prevent possible contamination of other cards in the event of a components failure; and the individual mounting of each card to the mounting plate improves dynamics and prevents undue stress or bending loads from being transmitted to the individual cards during use. Other components also are provided.

These and other aspects of the invention will be more fully understood by referring to the following detailed description and the accompanying drawings.

DETAILED DESCRIPTION

Figure 1:
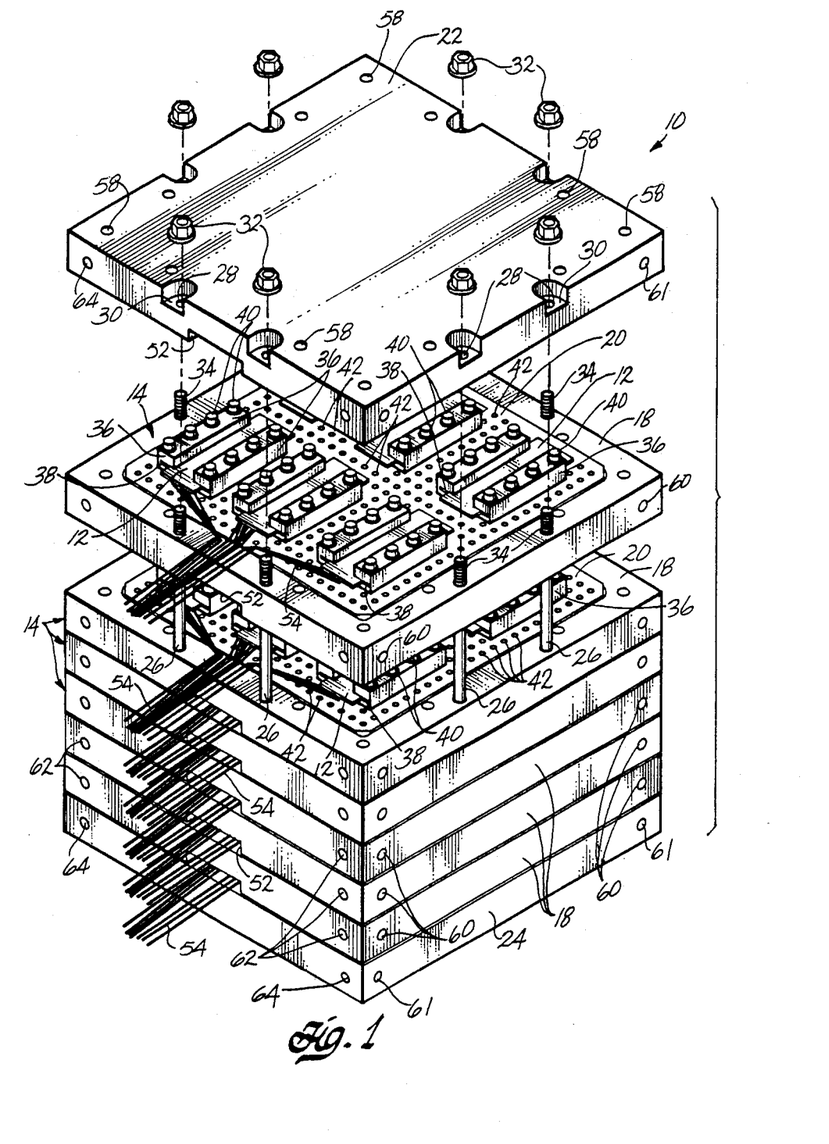
FIG. 1 is a fragmentary, partly exploded perspective view illustrating one embodiment of a modular test fixture according to principals of this invention.

FIG. 1 is a partly exploded perspective view illustrating a modular, multi-layer test fixture 10 for use in vibration and shock testing of components such as printed circuit cards 12. The test fixture comprises a plurality of identical circuit card-mounting trays 14 stacked one upon the other to form a vertical stack. Each card-mounting tray comprises a rigid rectangular outer frame 18 and a rigid rectangular card-mounting plate 20 affixed to the outer frame and held within the outer boundary formed by the frame 18. An upper cap plate 22 and a lower cap plate 24 are mounted at the top and bottom of the stack. Separate pairs of upright rigid alignment pins 26 are carried on each side of the lower cap plate. The pins extend through corresponding holes in each side of each outer frame 18 of the stacked mounting trays. The upper ends of the alignment pins extend through corresponding holes 28 which open through separate pairs of recessed regions 30 on each side of the upper cap plate 22. Internally threaded fasteners 32 are fastened to externally threaded upper end portions 34 of the alignment pins and are tightened against the corresponding recessed regions 30 of the upper cap plate for holding the trays together as a rigid unit.

The circuit cards 12 are each mounted to the upper surface of the card-mounting plate 20 by a separate pair of card-mounting clamps 36 secured to opposite faces of each circuit card. The opposite edges of each circuit card fit into opposing, inwardly facing slots 38 extending along the inside faces of each pair of clamps. Rows of fasteners 40 spaced apart along outer portions of the clamps are aligned with separate holes 40 in the mounting plate. The fasteners are tightened into corresponding holes in the mounting plate for applying a controlled amount of pressure to opposite edges of each card for rigidly securing the cards to the upper surface of the card-mounting plate. Printed circuit cards of varying sizes can be mounted to the card-mounting plate. Within the surface area of each mounting plate, the number of cards mounted to the plate can be varied depending upon the size of each card and the space occupied by its associated clamping means.

Once the circuit cards are mounted to each plate, the individual card-mounting trays are stacked together, with the upper and lower cap plates mounted above and below the stack. The fasteners 32 are then tightened to hold the fixture together as a rigid unit. The completed fixture is mounted to an external shaker (not shown) for subjecting the circuit cards in the fixture to multiple-axis vibration and shock testing familiar to those skilled in the art.

Figure 2:
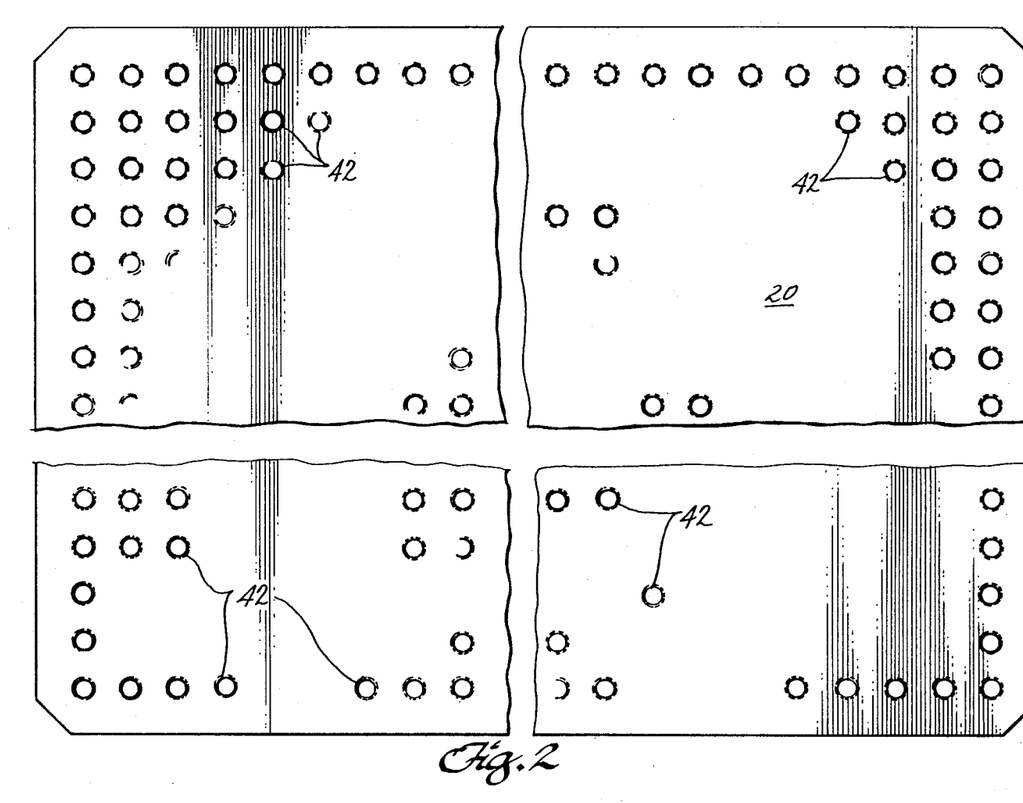
FIG. 2 is a fragmentary top plan view illustrating a card-mounting plate of this invention.

Detailed construction of components of the fixture is understood best by referring to FIGS. 2 through 6. FIG. 2 illustrates the card-mounting plate 12 which comprises a generally rectangular rigid metal plate on which the mounting holes 42 are arranged in a preselected two-dimensional array. The mounting holes are screw-threaded so that the fasteners 40 for the mounting clamps can be threaded into selected mounting holes in the array. In a preferred embodiment, the mounting plate is square in shape and the mounting holes are arranged in a square array, i.e., in uniformly spaced apart and parallel rows with adjacent holes in each row being uniformly spaced apart by the same distance as the spacing between adjacent rows. The plate is preferably made from aluminum; and in a preferred embodiment, the plate is about 11.5 inches square, 0.5 inch thick, and the mounting holes are spaced apart with a 0.5 inch on-center spacing.

Figure 3:
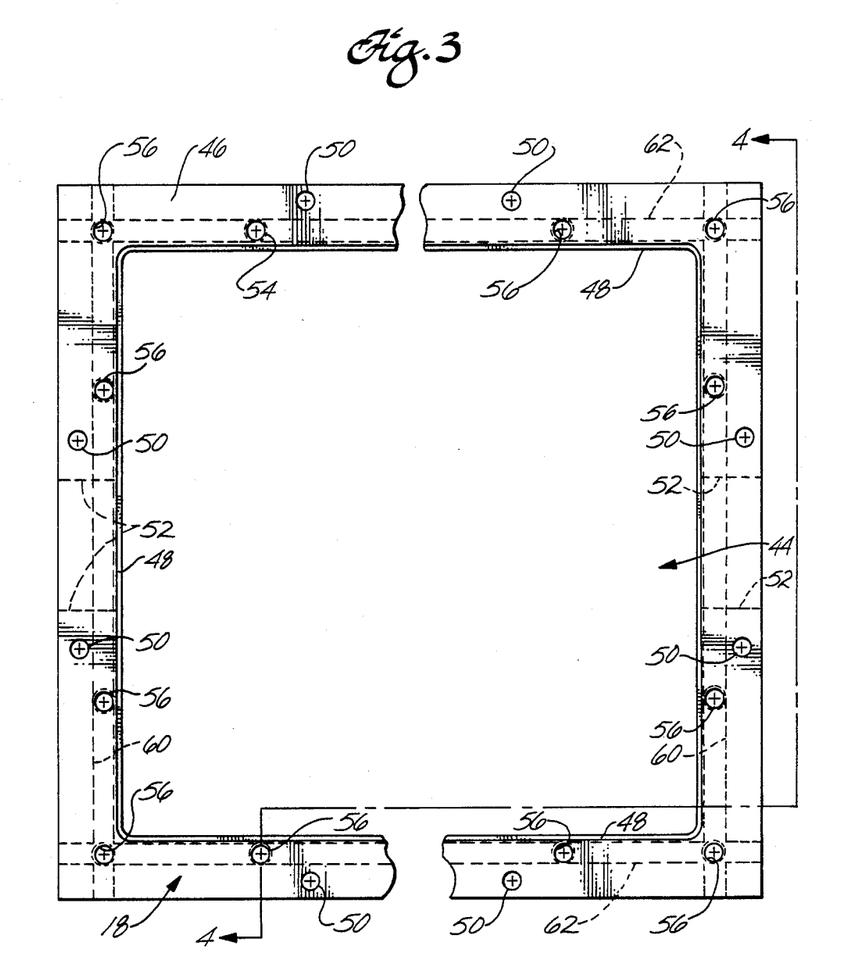
FIG. 3 is a fragmentary top plan view of an outer frame for a mounting plate.
Figure 4:
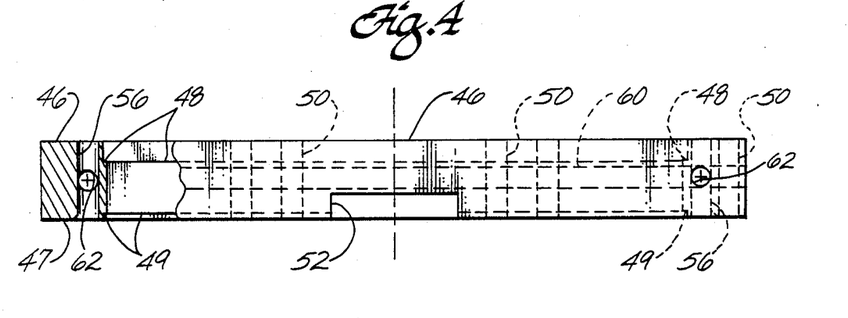
FIG. 4 is a side elevation view, partly in cross-section, taken on line 4—4 of FIG. 3.

FIGS. 3 and 4 illustrate construction of the metal outer frame 18 of each mounting tray. Each frame is rectangular in shape, and the long narrow legs of the frame enclose a large central rectangular opening 44. Each leg of the frame is a solid metal pieced with flat upper and lower faces 46 and 47 extending around the perimeter of the frame. A recessed shoulder 48 extends around the upper inside face of each leg of the frame to provide a support for the rectangular card-mounting plate 20. A recessed shoulder 50 is formed in the lower inside face of each leg of the rectangular frame and faces downwardly toward the frame below it in the stack. A pair of longitudinally spaced apart pin alignment holes 50 extend through a central portion of each leg of the frame. The alignment pins 26 shown in FIG. 1 extend through these pin alignment holes 50 when stacking the card-mounting trays one upon the other to form the fixture.

Separate rectangular slotted openings 52 extend as a channel through central lower portions of a pair of legs on opposite sides of the frame. The channels 52 provide access for connector cables 54 (see FIG. 1) leading to each of the circuit cards mounted to the card-mounting plate 20.

A plurality of fixture-mounting holes 56 are drilled vertically through the depth of the rectangular frame. These fixture mounting holes are preferably arranged in a pattern for use in extending long rods (not shown) through the frames of the stacked card-mounting trays for attaching the completed fixture to an external shaker. The mounting holes 56 are drilled on an identical pattern on each frame so that the holes on adjacent frames in the stack align vertically. The rods can then extend through the aligned holes when dropping the cube over the rods for fastening the completed fixture to the shaker. In the illustrated embodiment, a separate hole 56 is located at each corner of the frame, and a separate pair of longitudinally spaced apart holes are drilled in each leg at the same spacing between the holes located in the corners of the frame. Similar holes 58 extend in a rectangular pattern around the outer perimeter of the top cap plate 22 and the bottom cap plate 24 of the fixture for use in receiving the rods used in mounting the completed fixture to the shaker. The rods extending through the holes 56 and 58 for connecting the fixture to the shaker for rotating the fixture about a fixed first axis during vibration testing.

A pair of long holes 60 extend horizontally through the entire length of legs on opposite sides of each frame. These holes receive rods (not shown) for mounting the fixture for rotation about a fixed second axis. Pairs of long holes 61 extend in the same direction through legs on the same opposite sides of the top and bottom cap plates. These holes also are used for receiving rods for rotating the fixture about the second axis.

A pair of long holes 62 extend horizontally through the remaining legs on the opposite sides of the frame, and these holes receive rods (not shown) for mounting the fixture for rotation about a fixed third axis. Similar pairs of long holes 64 extend horizontally through legs on the same opposite sides of the upper and lower cap plates, also for mounting the fixture for rotation about the third axis.

In a preferred form of the invention, the mounting frame 18 is square in configuration, with each side of the frame approximately 13.8 inches long. The width of each leg of the frame is approximately 1.2 inches and the frame is approximately 1.5 inches thick. The width of the access channel 52 is approximately 2.5 inches with a height of approximately 0.5 inch. The drilled holes for mounting the rods for rotation about all three axes are approximately 0.44 inch in diameter. Each frame is preferably made of magnesium to reduce weight. The card-mounting plate is preferably press-fitted into the inside opening 44 of the frame in a tight pressure fit against the recessed shoulder 48 extending around the inside perimeter of the frame. The outer perimeter of the plate is preferably bonded to the frame by a suitable adhesive bonding agent. In addition, each plate preferably has a pair of upright dowels (not shown) at opposite diagonal corners of each frame to fit into corresponding openings in the frame stacked above it. When the stacked mounting trays are bolted together as a rigid unit, the dowel pin connections prevent rotational shifting of the trays.

Figure 5:
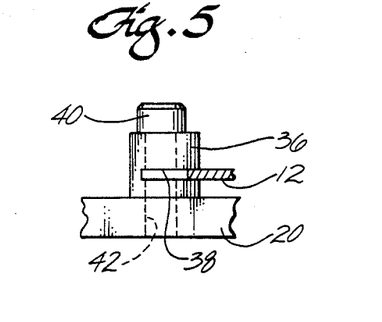
FIG. 5 is a fragmentary elevation view partly in cross-section, illustrating means for clamping a circuit card to the card-mounting plate.
Figure 6:
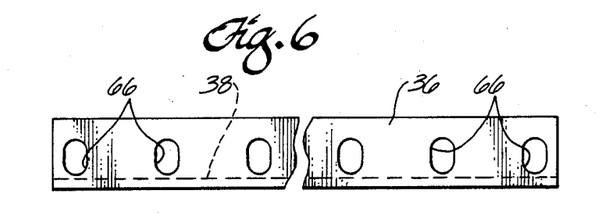
FIG. 6 is an top elevation view of a card-mounting clamp, taken on line 6—6 of FIG. 5.

FIGS. 5 and 6 best illustrate the card-mounting clamps 36, each of which comprises an elongated block of rectangular cross-section having a series of longitudinally spaced apart elongated holes 66 extending through the depth of the clamp. The narrow slot 38 for receiving the edge of the circuit card 12 extends the entire length of the clamp, in alignment with the holes which extend through the slotted region of the clamp. The holes are elongated to allow for adjusting the position of the clamp with respect to a selected row of holes 42 on the card-mounting plate 20, for allowing the blocks on opposite sides of the card to match the particular width of the card being mounted on the plate. The opposite edges of the card are inserted into the long slots along opposite inside faces of the pair of opposing clamps. The fasteners 40 are then inserted into the holes along the length of the clamp and are threaded into the aligned holes in the plate. The fasteners are then tightened for torquing them to a predetermined level. This causes the opposite portions of the clamp on opposite sides of the card to squeeze against the opposite faces of the card to apply a controlled amount of pressure to the edges of the card. The clamp is preferably made from a rigid non-conductive material. Phenolic resin is a preferred material which allows slight bending of the clamp on opposite sides of the slotted opening when pressure is applied by tightening the fasteners 40. The clamps hold the circuit cards in a rigid position with respect to the plate and avoid transmission of bending loads to the card during shock and vibration testing. The clamps can be made of any length and can be cut to size to match the length of each particular card being mounted to the card-mounting plate.

Thus, the invention comprises a multi-layer test fixture constructed of individual plates. Each mounting plate can hold any of a preselected number of circuit cards of varying sizes which are able to fit within the confines of the mounting plate. In one embodiment, each mounting plate holds one circuit card up to 10 inches square or multiples of smaller cards fitting within this area. Thus, total "in-house" customizing is provided in which boards of various sizes can be tested simultaneously. The fixture also allows connector cable access to each circuit card mounted on each mounting plate. The mounting plates are interchangeable which allows spare mounting plates to be loaded while others are in test to save time. The fixture can mount directly to the shaker in a vertical axis or to a slip-plate in a horizontal axis. The fixture is light in weight due to its combination of lighter metal elements made from aluminum, magnesium and composite materials, for example. The fixture provides maximum damping characteristics during use. Total axis change can be permitted without handling of PC boards or components. Each card is physically isolated to prevent possible contamination of other cards in the event of components failure. The modular design eliminates unwanted fixture mass often associated with other types of fixtures when small quantities test runs are required. In addition, as quantity requirements increase, additional PC board mounting tray modules can be added to the fixture assembly. The fixture does not require use of pneumatics or hydraulics which can potentially contaminate test components. All card attachment points use the method of mechanical torquing to provide necessary transmission of energy between the shaker or shock machine and the components being tested. For thermal chamber applications, air circulation spacer plates can be positioned between each mounting plate assembly to provide adequate air flow around the test components during use.

Although this invention has been described in relation to testing of printed circuit cards, it will be understood that the invention also is applicable to the testing of other components without departing from the scope of the invention.

What is claimed is:

1. A modular test fixture for use in testing of vibration and shock for printed circuit cards, or other components, comprising:
    a plurality of separate generally planar card-mounting plates, each card-mounting plate having a mounting surface within the confines of an outer boundary of the card-mounting plate, and means on the mounting surface for rigidly securing a preselected number of circuit cards of varying sizes to the mounting surface for holding the circuit cards generally within the plane and within the outer boundary of the card-mounting plates;
    the card-mounting plates with said circuit cards secured thereto being stackable, one upon the other, to form a multi-layer fixture containing circuit cards at different levels within the fixture;
    means for rigidly securing the stacked cardmounting plates together as a rigid unit sufficient for vibration and shock testing of the circuit cards securing to the card-mounting plates; and
    means for connecting the resulting fixture to an external shaker for imparting shock and vibration to the fixture for use in testing the circuit cards mounted within the fixture.

2. Apparatus according to claim 1 in which the means for securing the cards to the plates of each mounting surface comprise a two-dimensional array of mounting holes to which the circuit cards of varying sizes can be fastened.

3. Apparatus according to claim 2 in which the means for securing the cards to each plate further comprise elongated spaced apart card-mounting clamps each for fastening to an edge of a card of selected length, and fastening means carried on the clamp and fastened into selected mounting holes on the plate aligned with the fasteners on the clamps.

4. Apparatus according to claim 3 in which the fastening means comprise a row of spaced apart fasteners on each mounting clamp.

5. Apparatus according to claim 2 in which the mounting holes are arranged on the card-mounting surface in a uniformly spaced apart array, and in which the spacing of fasteners on the clamps matches the array of mounting holes on the plate.

6. Apparatus according to claim 1 including means for securing the cards to each card-mounting plate comprising separate elongated clamping means for releasably fastening to opposite edges of individual circuit cards of varying lengths, and fastening means on the clamping means for rigidly securing the clamping means to the mounting surfaces of the card-mounting plates.

7. Apparatus according to claim 6 in which the clamping means are adapted to mount an array of separate circuit cards in separate spaced-apart rows and columns on the mounting surface of each card-mounting plate.

8. Apparatus according to claim 6 in which the fasteners are torqued to tighten opposite faces of the clamping means to opposite edges of the circuit card to apply a controlled amount of pressure along the edges of each card for rigidly affixing the card to the rigid mounting plate.

9. Apparatus according to claim 1 in which each card-mounting plate has a rigid outer frame forming the boundary around the mounting surface of the plate, and the frames of the individual mounting plates rest on one another during stacking.

10. Apparatus according to claim 9 including means on each frame for releasably interlocking with an adjacent frame.

11. Apparatus according to claim 9 including spaced apart mounting pins on each side of the frames for extending through the frames to resist relative rotation of the frames and for use in aligning and fastening the stacked frames together as a rigid unit.

12. Apparatus according to claim 9 including at least one common cable slot on each frame for allowing cable access to the circuit cards mounted on each clamping means plate.

13. Apparatus according to claim 9 in which the means for connecting the resulting fixture to the shaker comprise multiple-axis holes in each frame for alignment with one another to hold rods extending through the holes in the frames to the shaker for use in multiple-axis mounting of the test fixture.

14. A modular test fixture for use in testing vibration and shock of printed circuit cards mounted to the fixture, comprising:
a plurality of separate generally planar card-mounting plates each having an array of card-fastening means generally in the plane of the mounting plate for rigidly securing a preselected number of circuit cards of varying sizes generally within the plane of the card-mounting plates;
means for stacking the individual card-mounting plates with the circuit cards attached thereto to form a rigid multi-layer fixture sufficient for vibration and shock testing of circuit cards mounted at different levels within the fixture; and
means for connecting the resulting fixture to an external shaker for imparting shock and vibration to the fixture for use in testing the circuit cards mounted within the fixture.

15. Apparatus according to claim 14 in which the card-fastening means include a two-dimensional array of mounting holes on the mounting plate and to which the circuit cards of varying sizes can be fastened.

16. Apparatus according to claim 15 in which each card-mounting plate further comprises a rigid outer frame forming the boundary around each plate, and in which the frames of the individual mounting plates rest on one another during stacking and are rigidly secured to one another as a fixed rigid unit, with the circuit cards fastened to the card-mounting plates at different levels within the fixtures, each level generally being within the plane defined by a corresponding outer frame.

17. Apparatus according to claim 16 including separate elongated spaced apart card-mounting clamps each for fastening to a respective edge of a circuit card, and fastening means carried on each clamp and fastened into selected mounting holes on the card-mounting plate aligned with the fasteners on the clamps.

18. Apparatus according to claim 14 in which the means for applying said pressure to the peripheral portions of the plates comprise separate outer frames secured to the plates and rigidly fastened together to form said fixture.

19. Apparatus according to claim 14 in which the stacked card-mounting plates with the circuit cards attached thereto are secured together by applying pressure to peripheral portions of the card-mounting plates to form said rigid test fixture.

20. Apparatus according to claim 19 in which the pressure is applied to peripheral portions of the plates independently of contact with the circuit cards under test.

21. A method for vibration and shock testing of printed circuit cards, comprising:
rigidly securing one or more printed circuit cards to each of a plurality of generally planar card-mounting plates,
stacking the card-mounting plates with the circuit cards attached thereto to form a multi-layer fixture,
thereafter securing the stacked card-mounting plates together to form a rigid test fixture with the mounted circuit cards held at different levels within the fixture, and
fastening the fixture to a shaker for imparting vibration or shock to the fixture for testing the cards mounted within the fixture.

22. The method according to claim 21 including testing various sizes of circuit cards simultaneously.

23. The method according to claim 22 including mounting a plurality of different sizes of circuit cards to clamping means fastened in spaced apart columns and rows to a mounting surface of each cardmounting plate, including adapting the length of each clamp and the spacing between opposite sides of the clamp for each circuit card to the size and shape of the circuit card for use in adapting the mounting of each circuit card within the confines of the card-mounting plate.

24. The method according to claim 2 including rigidly but releasably fastening each circuit card to its card-mounting plate by applying a controlled amount of pressure along the opposite edges of each card.

25. The method according to claim 21 in which the stacked card-mounting plates, with the circuit cards attached thereto, are secured together by applying pressure to peripheral portions of the card-mounting plates to form said rigid test fixture.

26. The method according to claim 25 in which the card-mounting plates are stacked in parallel layers within the rigid test fixture.

27. The method according to claim 25 in which the pressure is applied to said peripheral portions of the plates independently of contact with the circuit cards under test.

28. The method according to claim 25 in which the means for applying said pressure to the peripheral portions of the plates comprise separate outer frames secured to the plates and rigidly fastened together to form said fixture.

29. The method according to claim 21 in which a variable number of said card-mounting plates can be secured together in said rigid test fixture.

30. A modular test fixture for use in testing vibration and shock for printed circuit cards, or other components, comprising:
a plurality of separate generally planar card-mounting plates, each card-mounting plate having a mounting surface and means on the mounting surface for rigidly securing one or more circuit cards to the mounting surface for holding the circuit cards generally within the plane of the card-mounting plates, each card-mounting plate having a rigid outer frame forming an outer boundary around the mounting surface of the plate;

the card-mounting plates with said circuit cards secured thereto being stackable, with the frames of the individual mounting plates resting on one another during stacking, to form a multi-layer fixture containing circuit cards at different levels within the fixture;

means for rigidly securing the rigid outer frames together for forming the stacked card-mounting plates as a rigid fixture sufficient for vibration and shock testing of the circuit cards secured to the card-mounting plates; and means for connecting the outer frame members of the resulting fixture to an external shaker for imparting shock and vibration to the fixture for use in testing the circuit cards mounted within the fixture.

31. Apparatus according to claim 30 in which the means for securing the cards to the plates of each mounting surface comprise a two-dimensional array of mounting holes to which the circuit cards of varying sizes can be fastened.

32. Apparatus according to claim 31 in which the means for securing the cards to each plate further comprise elongated spaced-apart card-mounting clamps each adapted for fastening to an edge of a card of selected length, and fastening means carried on the clamp and fastened into selected mounting holes on the plate aligned with the fasteners on the clamps.

33. Apparatus according to claim 32 in which the fastening means comprise a row of spaced-apart fasteners on each mounting clamp.

34. Apparatus according to claim 31 in which the mounting holes are arranged on the card-mounting surface in a uniformly spaced-apart array, and in which the spacing of fasteners on the clamps matches the array of mounting holes on the plate.

35. Apparatus according to claim 30 including means for securing the cards to each card-mounting plate comprising separate elongated clamping means adapted for releasably fastening to opposite edges of individual circuit cards of varying lengths, and fastening means on the clamping means for rigidly securing the clamping means to the mounting surfaces of the card-mounting plates.

36. Apparatus according to claim 35 in which the clamping means are adapted to mount an array of separate circuit cards in separate spaced-apart rows and columns on the mounting surface of each card-mounting plate.

37. Apparatus according to claim 35 in which the fasteners are torqued to tighten opposite faces of the clamping means to opposite edges of the circuit card to apply a controlled amount of pressure along the edges of each card for rigidly affixing the card to the rigid mounting plate.

38. Apparatus according to claim 30 including means on each frame for releasably interlocking with an adjacent frame.

39. Apparatus according to claim 30 including spaced-apart mounting pins on each side of the frames for extending through the frames to resist relative rotation of the frames and for use in aligning and fastening the stacked frames together as a rigid unit.

40. Apparatus according to claim 30 including at least one common cable slot on each frame for allowing cable access to the circuit cards mounted on each card-mounting plate.

41. Apparatus according to claim 30 in which the means for connecting the resulting fixture to the shaker comprise multiple-axis holes in each frame for alignment with one another to hold rods extending through the holes in the frames to the shaker for use in multiple axis mounting of the test fixture.

42. A modular test fixture for use in testing vibration and shock of printed circuit cards mounted to the fixture, comprising:

a plurality of separate generally planar card-mounting plates, each card-mounting plate having a mounting surface and means on the mounting surface for rigidly securing one or more circuit cards to the mounting surface for holding the circuit cards generally within the plane of the card-mounting plate;

means for stacking the individual card-mounting plates, with the circuit cards attached thereto, to form a rigid multi-layer fixture sufficient for vibration and shock testing of circuit cards mounted at different levels within the fixture, said card-mounting plates being held rigidly with respect to one another in said fixture independently of contact with the individual circuit cards mounted to the individual card-mounting plates; and means for connecting the resulting fixture to an external shaker for imparting shock and vibration to the fixture for use in testing circuit cards mounted within the fixture.

43. Apparatus according to claim 42 in which each card-mounting plate further comprises a rigid outer frame forming the boundary around each plate, and in which the frames of the individual mounting plates rest on one another during stacking and are rigidly secured to one another as a fixed rigid unit thereby forming said fixture.

44. Apparatus according to claim 42 including separate elongated spaced-apart card-mounting clamps each adapted for fastening to a respective edge of a circuit card, and fastening means carried on each clamp and fastened into selected mounting holes on the card-mounting plate aligned with the fasteners on the clamps.

45. Apparatus according to claim 42 in which the stacking means includes means for applying pressure to peripheral portions of the card-mounting plates to form said rigid test fixture.

* * * * *

UNITED STATES PATENT AND TRADEMARK OFFICE
CERTIFICATE OF CORRECTION

PATENT NO. : 4,912,980
DATED : April 3, 1990
INVENTOR(S) : Daniel L. Baughn

It is certified that error appears in the above-identified patent and that said Letters Patent is hereby corrected as shown below:

Column 2, line 30, change "principals" to
-- principles --.
Column 2, line 40, before "top" change "an" to -- a --.

Column 5, lines 53,54, change "quantities" to
-- quantity --.

In the Claims

Column 6, line 20, change "cardmounting" to
-- card-mounting --.
Column 6, line 22, change "securing" to -- secured --.

Column 7, line 15, delete "clamping means" and insert therefor -- card-mounting --.

Column 8, line 26, change "cardmounting" to
-- card-mounting --.
Column 8, line 32, change "claim 2" to -- claim 22 --.

Signed and Sealed this

Thirty-first Day of December, 1991

Attest:

HARRY F. MANBECK, JR.

*Attesting Officer*   *Commissioner of Patents and Trademarks*